United States Patent [19]
Firnberg et al.

[11] Patent Number: 5,374,405
[45] Date of Patent: Dec. 20, 1994

[54] ROTATING FLUIDIZED BED REACTOR WITH ELECTROMAGNETIC RADIATION SOURCE

[75] Inventors: Dow Firnberg, Creskill, N.J.; James R. Fehlner, Salem Township, Wayne County, Pa.

[73] Assignee: Inrad, Northvale, N.J.

[21] Appl. No.: 728,880

[22] Filed: Jul. 12, 1991

[51] Int. Cl.$^5$ .............................................. B01J 19/12
[52] U.S. Cl. ................................ 422/186.3; 422/186; 422/139; 422/143
[58] Field of Search .............. 422/139, 143, 186, 186.3

[56] References Cited

U.S. PATENT DOCUMENTS

| | | | |
|---|---|---|---|
| 4,161,103 | 7/1979 | Horgan | 60/39.35 |
| 4,177,636 | 12/1979 | Horgan | 60/39.35 |
| 4,277,938 | 7/1981 | Belke | 60/39.35 |
| 4,282,009 | 8/1981 | Belke | 48/61 |
| 4,338,781 | 7/1982 | Belke | 60/39.35 |
| 4,343,624 | 8/1982 | Belke | 48/61 |
| 4,351,707 | 9/1982 | Turro | 204/158 |
| 4,693,189 | 9/1987 | Powers | 110/347 |
| 4,804,146 | 2/1989 | Nied | 241/5 |
| 4,954,320 | 9/1990 | Birmingham et al. | 422/186.04 |
| 4,966,759 | 10/1990 | Robertson et al. | 422/186 |
| 4,971,664 | 11/1990 | Turro | 204/158.12 |
| 4,971,687 | 11/1990 | Anderson | 210/85 |
| 4,990,311 | 2/1991 | Hirai et al. | 422/4 |
| 5,024,741 | 6/1991 | Maya | 204/157.22 |
| 5,116,582 | 5/1992 | Cooper et al. | 422/186.3 |

OTHER PUBLICATIONS

Yue, P. L., "Studies of Photoreactions in Heterogeneous Photoreactors", *Photocatalysis and Photoreactors*, (1985), pp. 575–585.

Socha, R. F., "Fluid-Bed Studies of Olefin Production from Methanol", ACS Symposium Series 328 (1987), pp. 34–41.

Fischer, M., "Industrial Applications of Photochemical Syntheses", Agew. Chem. Int. Ed. Engl. 17 (16–26) 1978.

Turro, N. J., "Photo. of n-Alkanes Adsorbed on Pentasil Zeolites", J. Org. Chem. 53, 3731–35 (1988).

Schnitzlein, M. G., "Flow Char. High-Vel. Fl. Beds Using Pressure Fluct.", C.E.S., vol. 41, No. 10, pp. 2605–2614 (1988).

Gal, E., "Dust Filtration in Granular Beds", UMI Dissertation Info. Serv. (1984).

*Primary Examiner*—Donald P. Walsh
*Assistant Examiner*—Daniel Jenkins
*Attorney, Agent, or Firm*—Stroock & Stroock & Lavan

[57] ABSTRACT

A rotating fluidized bed reactor in which inert solid particles are held in place by centrifugal forces. The reactor includes a rotating porous bed vessel drum within a plenum vessel and the drum rotates to hold the solid particles at the side thereof. Gas is introduced through the walls of the drum and can be drawn off at the top. An electromagnetic radiation source can be included within the drum for promoting photochemical reactions. The solid particles can be inert particles that are loaded with reactant which reacts with the gas stream and/or from the electromagnetic radiation. In other embodiments of the invention, the particles do not contain reactant and reactant is provided within the gas stream only. Such a rotating bed reactor is suitable for use with both batch and continuous flow through processes.

28 Claims, 5 Drawing Sheets

ROTATING FLUIDIZED BED REACTOR WITH ELECTROMAGNETIC RADIATION SOURCE

BACKGROUND OF THE INVENTION

The invent/on relates generally to a fluidized bed reactor and more particularly to a rotating fluidized bed photochemical reactor in which the solid particles of the bed are held in a rotating drum by high centrifugal fields in order to substantially eliminate entrained particles from the fluidizing gas flow. Therefore, the invention eliminates the need for cyclones and other trapping devices that are necessary to return entrained particles to a conventional gravity based bed. It also provides better control of bubble size in the bed, increases rates of reaction and provides many additional advantages compared to conventional beds.

Conventional fluidized bed chemical reactors employ a static bed of particulate solid material to catalyze chemical reactions. The particles are contained in a cylindrical or rectangular chamber. Air or another fluidizing gas in addition to an optional additional reactant gas can be introduced into a plenum chamber under pressure and forced upwardly through a diffusing medium such as a membrane or grate into the chamber containing the particulate solid material. The solid material can be either inert or can include solid reactant combined with inert particles.

The operation of conventional fluidized bed reactors is characterized by increasing the pressure of the gas flowing upward into the fluidizing chamber until the particles become fluidized. The pressure required to accomplish this objective is determined, in part, by the nature and degree of fineness of the particles to be fluidized. Other influencing factors are the depth of the bed and the size, number and design of the plenum chamber compartments and passages into the superimposed fluidizing chamber.

The rate at which a chemical reaction takes place in a fluidized bed depends, in large part, on the rate at which the reactants are brought together, the rate at which heat is supplied or removed from the bed and the rate at which the reaction products are removed. Heretofore, the rate at which the fluidizing gas can be blown through a conventional fluidized bed chemical reactor has been limited. As a result, the flow rate of the fluidizing agent through the particulate bed could not be increased because this would blow the particles out of the bed.

One method for increasing the forces that retain reactant particles in a fluidized bed hydrogen production system is described in U.S. Pat. No. 4,343,624, the contents of which are incorporated herein by reference. U.S. Pat. No. 4,343,624 describes rotating a bed including reactant particles mixed with inert particles and introducing a fluidizing gaseous agent into the bed from the bed periphery to oppose centrifugal force pushing the bed particles outwardly toward the bed periphery. The extent of the centrifugal force and consequently the force retaining the particles and opposing the drag force from the fluidizing gas can be controlled by adjusting the speed of bed rotation. Although such an approach increases flexibility in fluidizing gas flow rates, such an apparatus has not been contemplated for conducting a broad range of chemical reactions.

Rotating fluidized bed combustion chambers are also known and are described in U.S. Pat. Nos. 4,161,103, 4,177,636, 4,277,938 and 4,338,781. Similarly, a rotating fluidized bed gasifier system is described in U.S. Pat. No. 4,282,009. The contents of each of these patents are incorporated herein by reference. These rotating chambers are also limited in application and have not been contemplated for use in a broad range of fluidized bed reactions.

Photochemical reactions are important in the synthesis of many commercially significant compounds. Some examples of photochemical reactions include photochlorination, sulfochlorination and sulfoxidation of alkanes, photorearrangements, such as in the synthesis of vitamin $D_3$, photooxygenization and photonytrosation of cyclohexane. However, photochemical reactions are typically run in solution, which leads to processing problems, such as obtaining high selectivity in the reactions. See, Fisher, M., *Angew. Chem. Int. Ed. Engl.*, 17, 16 (1978).

It is desirable to conduct photochemical reactions on solid surfaces. For example, some solid particles act as catalytic surfaces for the photocleavage of water followed by reduction of compounds such as nitrogen to ammonia and alkenes to alkanes. Particles with pores, channels or chambers are capable of controlling the regio- and/or steroselective outcome of reactions. One example is the photochlorination of long chain alkanes absorbed on ZSM-5 zeolites yield more than 50% and as high as 80% chlorination on the terminal carbons of the mono-chlorinated product. This is compared to 10% terminal chlorination in solution photochemistry (Turro, N. J., Fehlner, J. R., Hessler, D. P., Welsh, K. M., Ruderman, W., Firnberg, D., and Braun, A. M., *J. Org. Chem.*, 53, 3731 (1988)). The terminal chlorination of hydrocarbons absorbed in zeolites is also discussed in U.S. Pat. No. 4,971,664, the contents of which are incorporated herein by reference. Enrichment of magnetic isotopes has also been observed in the photodecomposition of compounds adsorbed on silica, as described in U.S. Pat. No. 4,351,705, the contents of which are incorporated herein by reference. However, each of these known photochemical reactions are limited by conventional fluidized bed technology and have not become commercially significant by reason of the low efficiency of reaction obtained thereby.

Conventional fluidized bed technology used for photochemical reactions typically includes the use of cylindrical or parallel plate fluidized bed reactors. The latter has been demonstrated to be more efficient than the former, but with quantum efficiencies of only about 5 to 10 percent. (Yue, P. L. *Photoelectrochemistry, Photocatalysis and Photoreactors*, M. Schiavello, Ed., D. Reidel Publishing Col, 575 (1985)). One drawback which eliminates the quantum efficiency of conventional fluidized bed photochemical reactors is that the bottom region of the bed tends to be packed about 3 times more densely than the top region of the bed. A clearly defined interface has been shown to exist between the two sections. (Schnitzlein, M. G., Weinstein, H., *Chem. Engr. Sci.*, 43, 2605 (1988)). It is difficult to use light effectively in a conventional non-homogeneous bed. Another drawback of parallel plate fluidized bed reactors is that the bed must be irradiated from outside of the reactor. If high energy light in the UV region is required, the bed must be fabricated with quartz windows. This can undesirably increase construction cost and interfere with the ability to effectively utilize all of the available light.

Accordingly, a fluidized bed reactor that can overcome the deficiencies of conventional chemical reactors is desirable. Furthermore, a fluidized bed reactor that can run photochemical reactions and that avoids the deficiencies of conventional parallel plate and cylindrical fluidized bed photochemical reactors is also desired.

SUMMARY OF THE INVENTION

Generally speaking, in accordance with the invention, a rotating fluidized bed reactor is provided in which inert solid particles of the bed are held in place by centrifugal forces. The reactor includes a rotating porous bed vessel drum within a plenum vessel. The drum rotates to hold the solid particles to the sides thereof. Gas is introduced through the walls of the drum and is drawn off at the top. An electromagnetic radiation source can be included within the drum for promoting photochemical reactions. The solid particles can be inert particles that are loaded with reactant which reacts with the gas stream and/or electromagnetic radiation. In other embodiments of the invention, the particles do not contain reactant and reactant is provided within the gas stream only. Such a rotating bed reactor is suitable for use with both batch and flow through processes.

Accordingly, it is an object of the invention to provide an improved fluidized bed reactor capable of overcoming deficiencies of conventional reactors.

Another object of the invention is to provide an improved fluidized bed reactor having a decreased pressure drop, compared to conventional reactors.

A further object of the invention is to provide a fluidized bed reactor having increased reaction rates.

Still another object of the invention is to provide an improved fluidized bed reactor to more efficiently promote photochemical reactions on solid surfaces.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
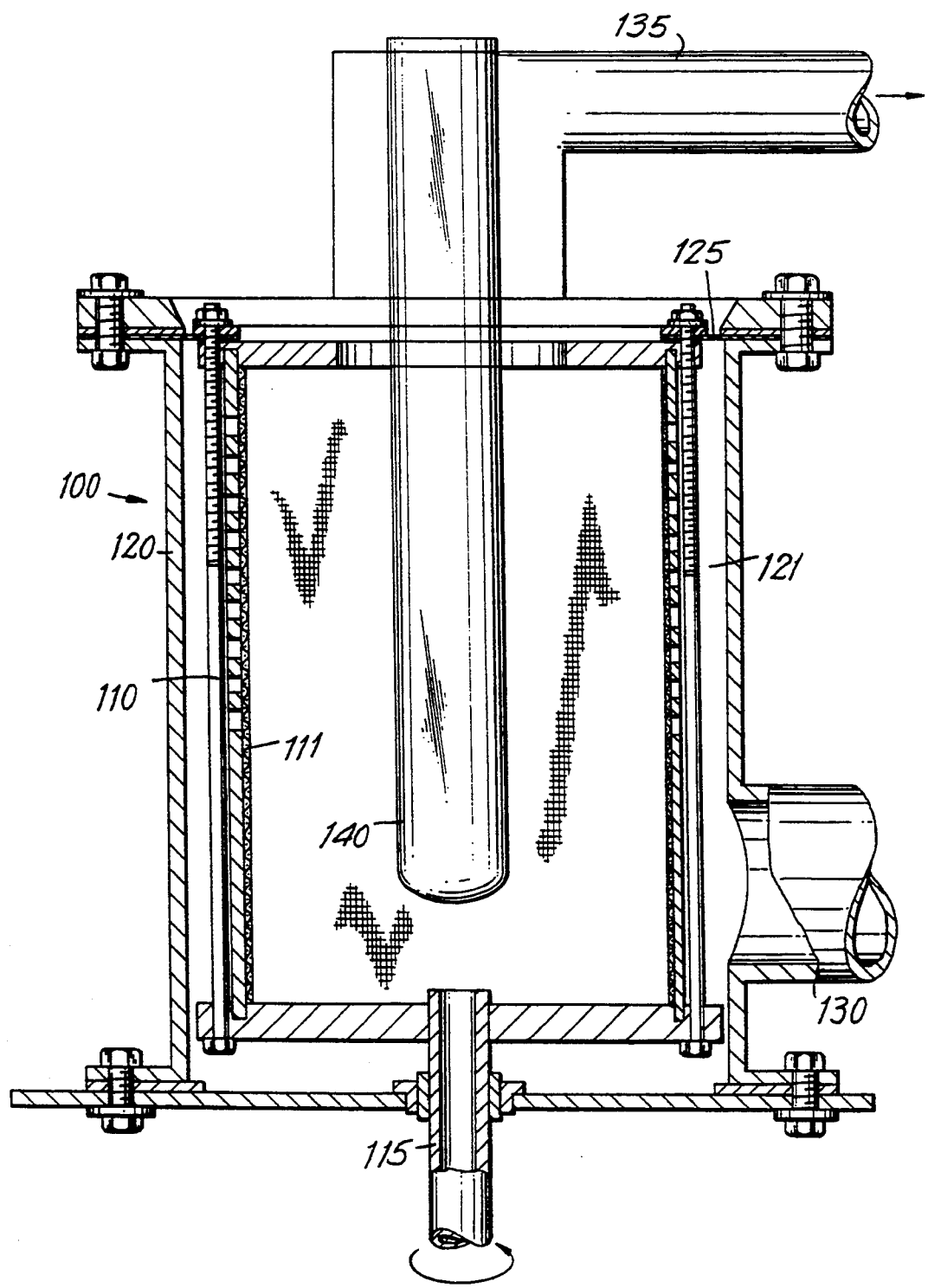
FIG. 1 is a front cross-sectional view of a rotating fluidized bed reactor in accordance with an embodiment of the invention.

The fluidized bed photochemical reactor (processor) of the present invention employs a rotating fluidized bed vessel which can include an electromagnetic radiation source at its center for the photochemical conversion of compounds adsorbed or absorbed on inert solid particles. Such a device provides quantum efficiencies many times those obtained from conventional cylindrical or parallel plate fluidized bed reactors. By rotating the fluidized bed, centrifugal fields several times the force of gravity can be generated to hold the particles in the bed. This eliminates the problem of entrained particles in the fluidizing gas flow. Consequently, there is substantially reduced need for cyclones or other trapping devices necessary to return entrained particles to conventional gravity based beds. Accordingly, rotating beds in accordance with the invention have fewer pollution problems.

The rotating fluidized bed reactors of the present invention provide other advantages, compared to conventional reactors. The void fraction in the bed, bed density and consequently the bubble size can be controlled with greater uniformity. Rotating fluidized bed reactors in accordance with the invention can also lead to lower pressure drops, higher rates of reaction and a decrease in the number of bed modules necessary for large system capacity. Shorter residence times are available and this will minimize abrasive wear on the catalyst particles and therefore increase the lifetime of the catalyst. By providing a lamp at the center of the bed, the maximum amount of available light is utilized, the need for expensive quartz windows is eliminated and particles are kept away from the radiation source.

A reactor in accordance with the invention includes a bed vessel drum that can rotate and force particles of the bed against the drum wall. Accordingly, the central core at the axis of rotation will lack particles which will all be pushed against the drum wall. Although the rotation rates will vary with the size of the reactor, rotation rates of 200 to 1000 RPM are preferred, with rates of 400 to 700 RPM even more preferred. The bed wall is preferably cylindrical and vertical or inclined to promote particles travelling up the sides of the vessel wall. The axis of rotation is preferably substantially vertical, but can also be horizontal or any other angle. The wall acts as a diffuser or distributor for the fluidizing gas and can be porous, perforated, screen-like, etc. The bed vessel can be rotated by coupling a shaft to the bottom or top of the drum, with gears, with a chain wheel and drive chain, with a belt and the like.

The drum is preferably located within a plenum vessel and gas should be introduced from the side of the plenum vessel and tangentially to the bed wall of the drum. The gas can enter either with the direction of drum rotation or against the direction of drum rotation, depending on the intended application. The top or bottom of the bed vessel should be coupled to a gas outlet and the gas can be recycled or processed further, depending on the type of reaction involved. Because of the strong forces acting on the particles, small sized particles as small as 10 to 15 μm and smaller can be employed with large gas flows and the small particles will not be blown out of the outlet. Larger particles such as silica particles of 100 to 250 mesh and particles as large as sand grains and larger can also be utilized with large gas flows and will not be blown out of the outlet.

A source of electromagnetic radiation such as UV light, visible light and infra red radiation can be included within the rotating bed vessel. The solid particles will not contact the source which need not be protected with transparent shielding. The type of source, such as a bulb, lamp or other source will be determined in part by the requirements of the reaction.

In one embodiment of the invention, reactant will be loaded on inert solid catalytic particles which will be rotated and fluidized in the reactor. The reactant on the particles will react with at least one component of the fluidizing gas stream and the reaction product on the particles and/or in the outlet gas stream is collected. In another embodiment of the invention, an electromagnetic radiation source is included to foster the reaction of reactant combined with catalytic particles or between the gas stream and reactant combined with catalytic particles. In another embodiment of the invention, the particles are catalytic and the radiation source helps cause a reaction of the source gas. Each of the processes can be run either as batch or continuous flow processes. Accordingly, rotating fluidized bed reactors in accordance with the invention operate differently than do rotating fluidized bed gasifiers, combusters or filters. Some examples of photochemical reactions that can be conducted with reactors in accordance with the invention include photochlorination, sulfochlorination and sulfoxidation of alkanes, photorearrangements, such as in the synthesis of vitamin $D_3$, photooxygenization and photonytrosation of cyclohexane and the catalytic cracking of petroleum compounds.

Examples of rotating fluidized bed reactors will be discussed in greater detail with reference to FIGS. 1 to 4. These examples are presented for purposes of illustration only and are not intended to be constructed in a limiting sense.

A rotating fluidized bed reactor 100 constructed in accordance with an embodiment of the invention is illustrated in FIG. 1. Reactor 100 includes a cylindrical plenum vessel 120 enclosing a rotatable cylindrical bed vessel drum 110 for containing the solid particles. A vertical wall 111 of drum 110 can be either porous or screen-like and a gas chamber 121 is defined between drum 110 and plenum vessel 120. Fluidizing gas is introduced through a gas inlet pipe 130 located towards the bottom of plenum vessel 120 and vertical wall 111 of drum 110 acts as a gas distributor or diffuser for gas to enter drum 110. Appropriate seals, such as a teflon seal 125 are included to prevent any loss of material.

Particulate matter is to be enclosed within drum 110 and will be forced against wall 111 due to the large centrifugal forces that are produced when drum 110 is rotated. Drum 110 is supported on a rotatable shaft 115 and is rotated thereby. After fluidizing gas is fed into reactor 100 through an inlet pipe 130 and passes through porous wall 111 of drum 110 and through particulate matter forced against the wall 111 the gas, including any product gas, ultimately exits through the top of drum 110 through an outlet pipe 135. Appropriate seals are included to prevent leakage.

Vertical wall 111 of drum 110 serves as a gas distributor for the bed and directs the gas flow inward through wall 111 and then through the bed particles. When the drag forces on the particles or granules of the bed balance the centrifugal forces, the bed becomes fluidized. Fluidization can be achieved over a large range of gas flow rates by changing the rotational speed of drum 110.

A reactor in accordance with the invention can be modified to permit the continuous addition and removal of reactor particles for use with reactions in which the product becomes adhered to the particles and must be removed therefrom. The particles can be added to and removed from the bed through ports located at the top, bottom or sides of the drum.

Reactor 100 also includes a light source 140 such as an ANALAMP mercury lamp positioned within rotatable drum 110. Light source 140 is selected to provide the electromagnetic radiation wavelength appropriate to the absorption characteristics of the reactants and the energy requirements of the reaction. In an alternative embodiment of the invention, the energy source for the radiation can be located outside of the bed and directed into the bed with an appropriate optical arrangement. For example, solar flux can be concentrated and directed into the bed with a series of mirrors and/or through the use of a fiber optic bundle.

A reactor in accordance with another embodiment of the invention can be run as a continuous operation. The reactor can include an inner plenum that is part of the rotating system and a second stationary plenum to be used for collecting solids from tubes inserted into the bed and penetrating out through the rotating plenum. The solids would be fed in through feed tubes which can be located at the top or bottom of the chamber. Alternatively, the solids can be added directly to the bed through a feed tube at the top of the bed, under pressure and the exposed particles can be collected through adjustable openings which can be positioned at the bottom of the bed.

The fluidizing gas for the reaction should typically be a relatively inert gas, such as nitrogen or a noble gas, in order to avoid problems such as the quenching of reaction intermediates when product on the particles is exposed. However, in other embodiments of the invention, reactant gases can be added to the fluidizing gas in appropriate concentrations. If any of the reaction constituents are corrosive, the bed should be constructed with appropriately corrosion resistant materials. The fluidizing gas can be removed from outlet 135 and filtered, if necessary and recirculated through a pump to bring it back up to appropriate pressure.

Product removal and workup procedures are determined by the characteristics of the desired products. If the product is a gas, it will be carried off with the fluidizing gas and then separated, before the fluidizing gas is recirculated. Under those conditions, the catalytic solid particles can remain in the bed until they lose their catalytic activity or effectiveness or become broken down by physical collisions in the bed. If the desired product is a liquid or solid adsorbed on or absorbed in the catalytic particles, the particles are removed from the bed and separated from the product. The solids can then be reloaded with fresh reactant and returned to the bed.

The dimensions of the bed can be adjusted to meet the particular requirements of the process being run. With the amount of solid remaining constant, a smaller diameter rotatable drum will lead to a thicker bed that is closer to the light source. A thicker bed increases the tension between particles near the center of the bed which leads to greater particle abrasion. Increasing the diameter of the drum will decrease the thickness of the bed and decrease particle abrasion. However, the light intensity per unit area at the surface of the particles will be decreased. Unless the drum is filled, there will be space between the light source and particle surface. The diameter of the plenum is established by the kinetics of the reaction, the required capacity and the bed thickness. The gas temperature can be controlled to control the kinetics of the reaction system.

The vertical height of the bed can be used to control the residence time of the particles in the bed when a continuous flow process is employed. The height of the plenum is established by the residence time of the particles. If the particles are fed in at the top of the bed and are removed at the bottom, the residence time will be determined by how long it takes for the particles to reach an exit port. The bed height can be established by desired exposure time.

Rotating fluidized beds in accordance with the invention have highly efficient filtration properties and can be used as effective gas filters. The direction of gas entering the plenum should be with the direction of rotation of the drum. This can increase the efficiency of filtration. Submicron particles and droplets in a gas stream can be removed efficiently from the fluidizing gas with a bed that can be formed of relatively large particles such as sand, polymer beads or ceramic beads. The particles are preferably electrical insulators and ceramic beads are highly suitable for filtering gas flows at elevated temperatures. Once captured in the bed, the submicron particles and/or droplet material can be photochemically reacted either alone or in combination with a reactant gas. Particulate catalysts can be useful for the photodetoxification of halogenated hydrocarbons and the reactor of the invention can be useful for the photodecontamination of polluted air. This can provide important products and can also serve as a way to decontaminate material removed from polluted air. Bacteria and/or viruses can also be filtered from contaminated air and killed with irradiation.

Figure 2:
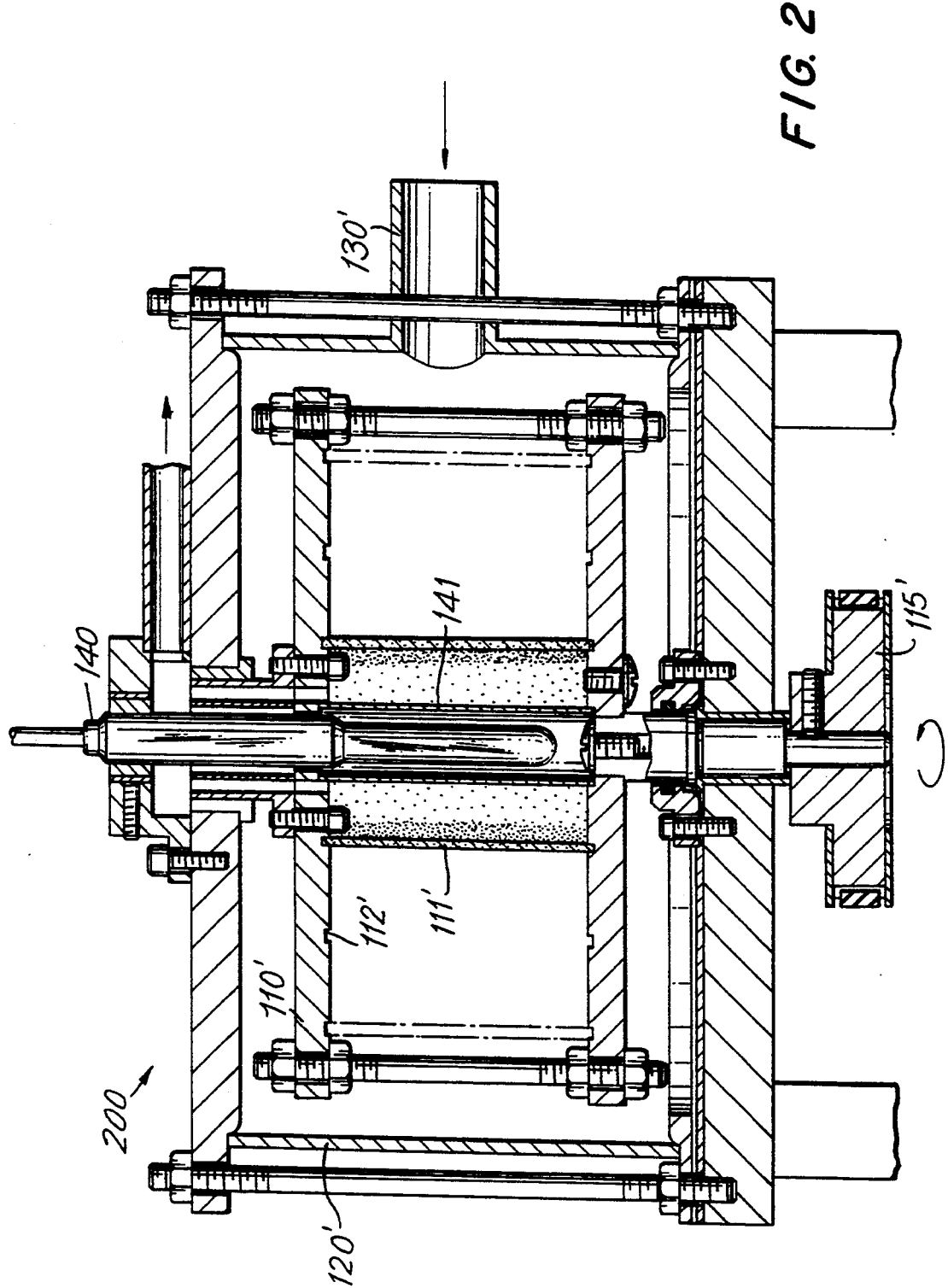
FIG. 2 is a front cross-sectional view of a rotating fluidized bed reactor in accordance with another embodiment of the invention.

A rotating fluidized bed photochemical reactor 200 is shown in FIG. 2. Reactor 200 is constructed similarly to reactor 100 and includes a gas inlet 130' and a plenum vessel 120' for delivering gas to a fluidized bed drum 110' and a rotatable shaft 115' for rotating drum 110'. However, drum 110' includes a removable distributor wall 111' that can be formed of a sintered stainless steel cylinder, for example. Drum 110' includes a plurality of circular notches 112' permitting the use of differently sized distributor walls 111'. In one embodiment of reactor 200, distributor walls 111' can be 2, 4 or 6 inches in diameter.

Reactor 200 also includes a lamp 140, enclosed in a transparent window that can be in the form of a quartz tube 141. Because quartz tube 141 is located within the reactor, rather than outside of the reactor, it can be made smaller than and therefore less expensive than conventional transparent fluidized bed windows. However, the transparent window is not always necessary because the particles will be against wall 111'.

Figure 3:
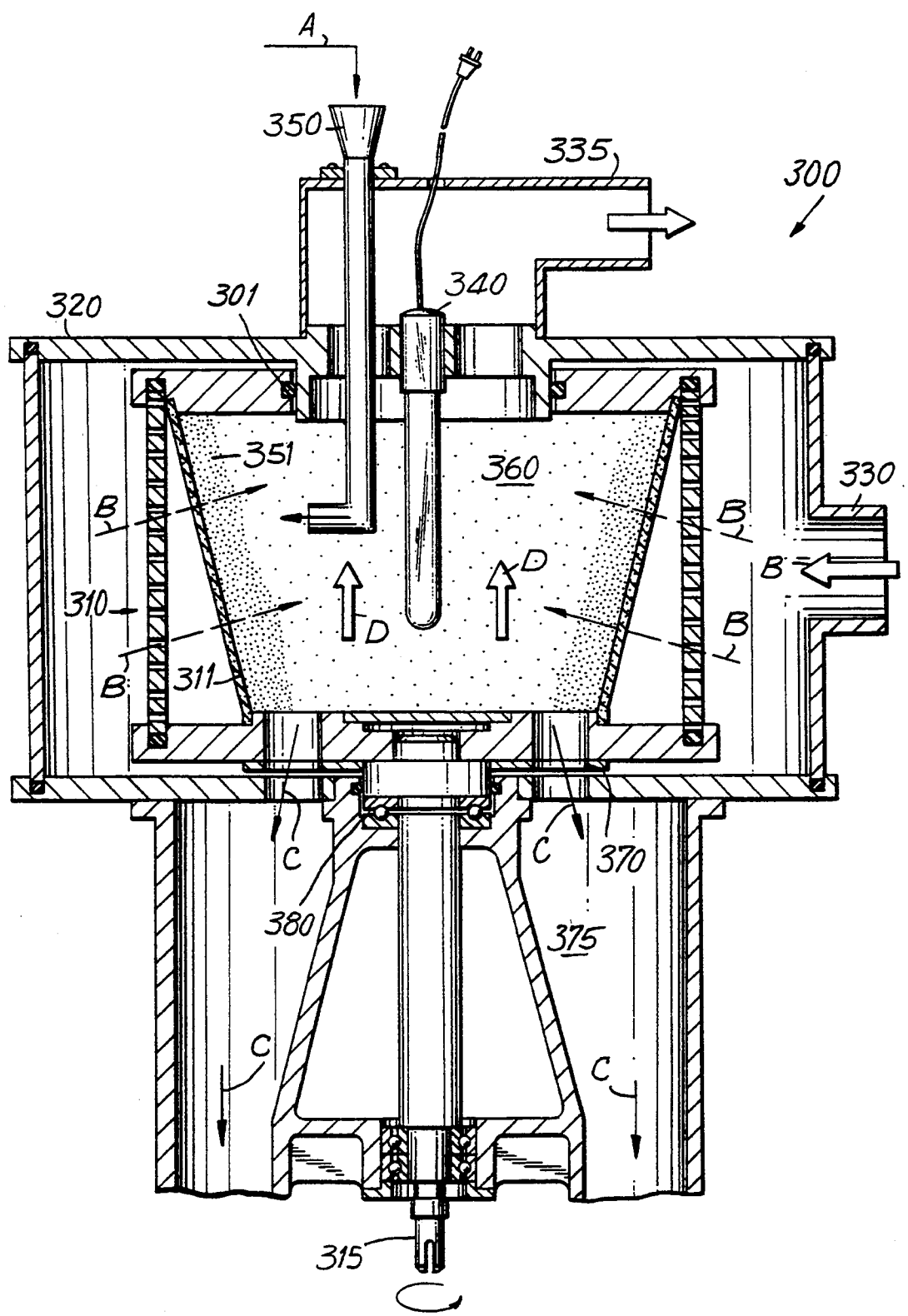
FIG. 3 is a front cross-sectional view of a continuous feed rotating fluidized bed reactor in accordance with another embodiment of the invention.

A continuous feed rotating fluidized bed photochemical reactor 300, in accordance with still another embodiment of the invention is shown in FIG. 3. Reactor 300 is similar to reactors 100 and 200 and includes a gas inlet pipe 330, a plenum vessel 320 and an exhaust pipe 335. Reactor 300 also includes a UV lamp 340, a drive shaft 315 and a plurality of seals 301. Broken arrows in FIG. 3 as well as in FIG. 4 show the direction of gas flow and solid arrows show the direction of the flow of solids.

A continuous flow of solid particles 351 that can include reactant for the fluidized bed are introduced at the top of the rotating bed through a particle feed nozzle 350 in the direction of an arrow A. Reactor 300 includes a cone shaped bed drum 310 that has an inclined side wall 311, rather than the vertical side wall of reactors 100 and 200. Inclined wall 311 of drum 310 make it easier for solid 351 in drum 310 to travel up the sides of drum 310 when drive shaft 315 is rotated. Wall 311 of drum 310 is porous and gas enters the bed therethrough in the direction of a plurality of arrows B.

During operation of continuous feed reactor 300, solids 351 are continuously added to drum 310 through particle feed nozzle 350 and exit through one or more adjustable discharging ports 370 in the direction of an arrow C, into a collecting chamber 375. Reactor 300 should include a plurality of appropriate bearings and seals 380 in order to prevent any loss of gas or solid. Exhaust gases exit in the direction of a plurality of arrows D and can be recycled or otherwise processed.

Figure 4:
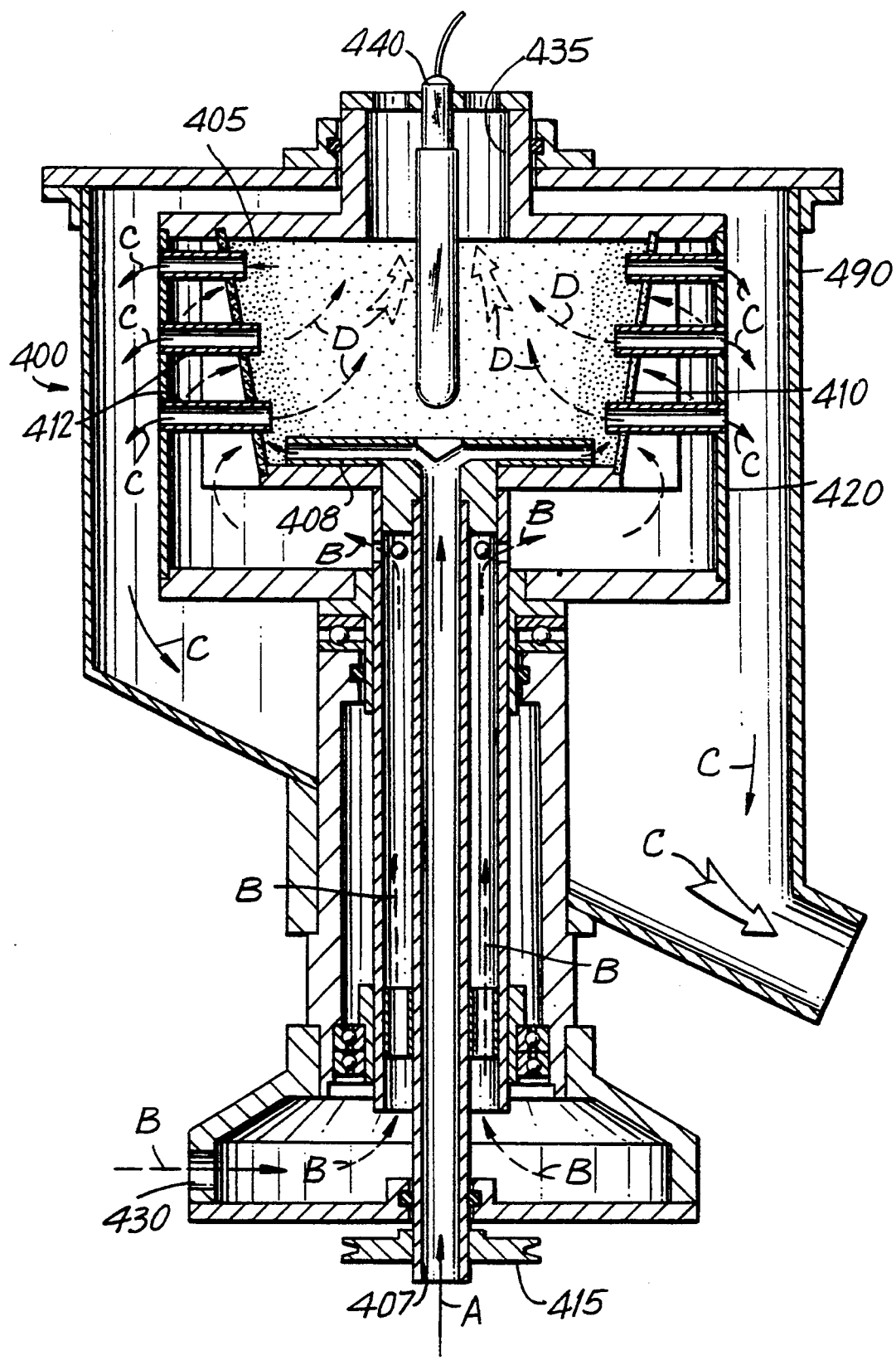
FIG. 4 is a front cross-sectional view of a continuous feed rotating fluidized bed reactor in accordance with another embodiment of the invention.

A continuous feed rotating fluidized bed photochemical reactor 400, constructed in accordance with still another embodiment of the invention is shown in FIG. 4. Reactor 400 includes a rotating plenum 420, located within a solids discharge plenum 490. A rotating inclined bed wall 410 formed of porous material is included within rotating plenum 420 and a drive shaft 415 is provided for rotating plenum 420 and consequently bed wall 410.

A flow of solids 405 are introduced through a solids inlet pipe 407 at the bottom of reactor 400 in the direction of an arrow A, to a rotating solids distributor 408 located at the bottom of bed wall 410. As drive shaft 415 rotates, solids 405 travel up inclined porous bed wall 410 and eventually exit through one of a plurality of solids discharge tubes 412, which extend through plenum 420 and bed wall 410, in the direction of a plurality of arrows C.

Fluidizing gas, such as air, enters through a fluidizing gas inlet 430, located at the bottom of reactor 400 and travels in the direction of a plurality of broken arrows B. The gas then passes through inclined phorous bed wall 410, through solid particles 405 and exits reactor 400 through an exhaust gas outlet 435 in the direction of a plurality of arrows D.

The use of rotating fluidized bed photochemical reactors in accordance with the invention will be described more particularly, with reference to the following examples. These examples are presented for the purpose of illustration, and are not intended to be construed in a limiting sense.

EXAMPLE 1

Figure 5:
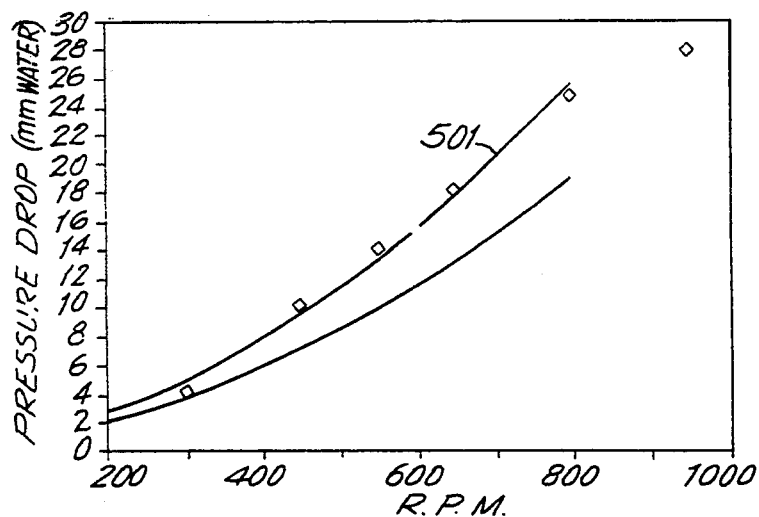
FIG. 5 is a graph showing change in pressure drop with the change in speed of rotation of a reactor drum constructed in accordance with an embodiment of the invention.

To demonstrate that a rotating fluidized bed reactor operates under a fluidizing regime, 50 grams of silica gel, 100 to 115 mesh, were placed into a rotating fluidized bed vessel of the type depicted in FIG. 2 and the vessel was rotated. The gas flow into the side wall of the vessel was set at a constant 27 liters per second and the pressure drop through the bed was measured as the rotational speed was varied from 300 to 1000 revolutions/min (RPM). The variation of pressure drop with the change in the speed of bed rotation at constant gas flow is shown in FIG. 5. The points represent actual data points and a curve 501 represents predicted values, calculated assuming the tangential velocity to be constant throughout the bed. Data points that are below curve 501 indicate fixed bed conditions and those above curve 501 indicate a fluidized bed. For this set of conditions, the bed converted from a fluidized bed to a fixed bed when the rotation rate exceeded about 700 RPM.

EXAMPLE 2

Figure 6:
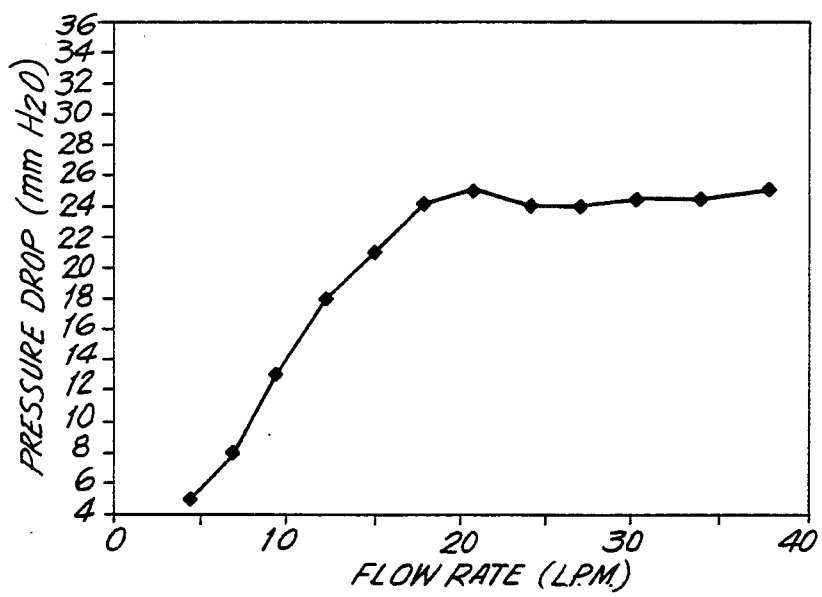
FIG. 6 is a graph showing the change of pressure drop with gas flow rate across a rotating bed reactor drum constructed in accordance with the invention.

To further demonstrate that the reactor operates under a fluidizing regime and to demonstrate the change in pressure drop across the bed with changes in gas flow rate at a constant bed rotation speed, silica having a size distribution of from 150 to 200 mesh was put into a rotating reactor of the type illustrated in FIG. 2 constructed in accordance with the invention. The bed was rotated at 450 RPM and the pressure drop over the bed was measured as the gas flow rate was varied from 4 to 40 liters per minute. The change in pressure drop with flow rate is shown in FIG. 6. As shown therein, the bed achieved fluidization at a gas flow rate of about 20 liters per minute and demonstrated acceptable fluidized bed characteristics.

Comparison Example 3

To provide characteristics of a conventional bed for comparison, dibenzyl ketone was absorbed on 150–200 mesh silica at 2% loading by weight. 60 grams of this loaded silica was placed in a parallel plate fluidized bed reactor. The bed was fluidized with nitrogen as a fluidizing gas and exposed with a 5 watt UV lamp using reflectors to assure that all of the light produced by the lamp was used to irradiate the bed to convert the dibenzyl ketone to diphenyl ethane and carbon monoxide. Silica blown out of the bed was constantly recirculated through the use of a cyclone to recapture particles. Samples were taken periodically during the experimental run, over 12 hours, extracted with ether and analyzed by gas chromatography. The results of this Example 3 are plotted as the plus sign shaped symbols in FIG. 7 and are set forth in Table 1 below. It was estimated that about 7% of the available light was utilized, based on theoretical estimates of conversion.

EXAMPLES 4 TO 7

As set forth in Table 1, below, different sample sizes having different mesh size silica inert particles were loaded with 2% dibenzyl ketone reactant and placed in a rotating fluidized bed photochemical reactor of the type illustrated in FIG. 2 constructed in accordance with the invention. The bed was fitted with a two inch diameter cylindrical gas distributor wall and the five watt lamp of Example 3 was used to irradiate the rotating bed particles from within. Examples 4 through 7 were conducted at a bed rotation rate of 500 RPM and the solid particles were fluidized with nitrogen as an inert fluidizing gas. Samples were collected over a period of from 2 to 6 hours by slowing down the speed of rotation or increasing gas flow to force solid out of an exit port. Work up and analysis were conducted as described in Comparison Example 3 and the results are set forth below in Table 1. The data from Example 4 are also plotted as the square shaped symbols in FIG. 7. Efficiencies for the conversion of dibenzyl ketone to diphenyl ethane vary between 20 and 40% and virtually no material was lost unintentionally from the bed during operation.

Figure 7:
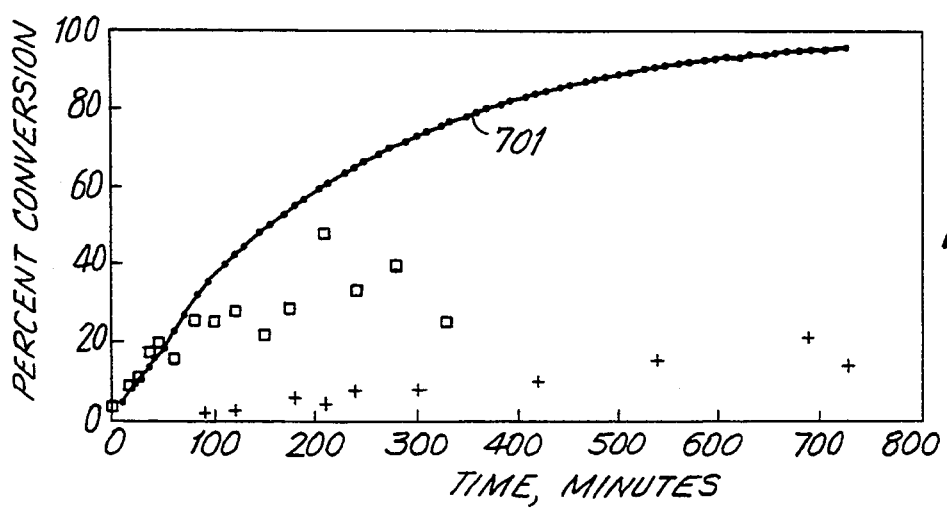
FIG. 7 is a graph showing the change of percent conversion of a photochemical reaction with time for both a conventional reactor and for a reactor constructed in accordance with the invention.

Referring to FIG. 7, the predicted conversion percentages are shown as a curve 701. As product accumulates, it absorbs the ultraviolet light which begins to slow down the reaction rate. The data from the rotating bed indicate that about 30% conversion can be achieved during a time duration of 100 and 200 minutes with a reactor in accordance with the invention. This value can only be achieved after over 700 minutes in a parallel plate reactor.

TABLE 1

| Photodecomposition of Dibenzyl Ketone on Silica in Parallel Plate and Rotating fluidized Beds | | | | | |
|---|---|---|---|---|---|
| Ex | Bed Type* | Mesh | Sample Size (g) | Time (min) | % Conv | Photoefficiency (%) |
| 3 | PP | 120–200 | 60 | 720 | 15 | 7 |
| 4 | RB | 100–200 | 60.2 | 330 | 42 | 21 |
| 5 | RB | 100–200 | 35 | 185 | 31 | 23 |
| 6 | RB | 150–200 | 42.3 | 180 | 27 | 39 |
| 7 | RB | 150–200 | 25.5 | 135 | 26 | 39 |

*PP — Parallel Plate Bed; RB — Rotating Bed

As used herein, photoefficiency will represent the ratio of observed conversion to maximum predicted conversion, assuming 100% use of light, multiplied by 100.

EXAMPLE 8

115 to 150 mesh silica gel inert particles were deactivated with water, loaded with 2% dehydrocholesterol, placed into a rotating fluidized bed reactor constructed in accordance with the invention and irradiated with UV light as in Examples 4–7. Samples were removed, extracted with methanol and analyzed by UV spectroscopy. The UV spectra showed that there was a significant shoulder in the spectra at 260 nanometers, indicating the formation of previtamin $D_3$ after 2 hours. Previtamin $D_3$ is an isomer of Vitamin $D_3$ and can be converted to Vitamin $D_3$ by conventional thermal rearrangement methods. Essentially no material was lost during operation of the reactor.

EXAMPLE 9

A ZSM-5 zeolite, having approximately 10 to 15 micron crystals was loaded with 2% dodecane by weight and placed into a rotating fluidized bed reactor constructed in accordance with the invention. The bed was rotated at 670 RPM and fluidized with gas at a flow rate of 21 liters per minute. Chlorine was added to the fluidizing gas at a rate of 14.8 ml/min. and the particles rotating in the reactor were irradiated with the 5 watt UV lamp of Examples 1–8. Samples were taken over a 2 hour period, extracted with methylene chloride and analyzed by gas chromatography. After 55 minutes, there was about a 59% conversion to primarily 1-chlorodecane and other less preferred chlorodecanes. Essentially no zeolite was lost from the bed during the two hours of operation. With proper zeolite crystals, the reactor can provide more than 50% of the preferred chlorodecane. In fact, with proper crystals, up to 80% of the monochlorododecanes will be 1-chlorododecane.

Comparison Example 10

A 0.2723 gram sample of the zeolite particles loaded with dodecane, of Example 9, and was fluidized in a conventional cylindrical reactor. The nitrogen fluidizing gas was introduced at 0.707 liters/min., chlorine gas was added at 1.5 ml/min. and the bed was irradiated with a 60 watt U.V. lamp. After a 4 minute exposure, there was 28% conversion, but only 0.0520 g of zeolite was recovered. This represents less than 20% of the starting weight.

As described above, a rotating fluidized bed reactor can provide the continuous photoconversion of materials such as compounds adsorbed or absorbed in solid particles at much higher photoefficiencies than with conventional photochemical fluidized beds and without the loss of solid.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A rotating fluidized bed chemical reactor, comprising:
    plenum means for delivering gas to a rotating fluidized bed;
    drum means, rotatable about a rotation axis thereof containing solid particles for a rotating fluidized bed, the drum means having an annular wall defining an inner surface and an outer surface, the annular wall positioned annularly around the rotation axis;
    the plenum means and the drum means being constructed and arranged so that the plenum means can deliver gas to the outer surface of the annular wall and the annular wall is constructed so that gas from the plenum means will pass through the annular wall;
    the drum means including a gas outlet so that gas from the plenum means that passes through the annular wall will exit from the gas outlet; and
    radiation means for providing electromagnetic radiation to the interior of the drum means from within the drum means.

2. The rotating fluidized bed reactor of claim 1, wherein the radiation means provides electromagnetic radiation to the interior of the drum means from within the drum means at substantially the rotation axis of the drum means.

3. The rotating fluidized bed reactor of claim 1, wherein the electromagnetic radiation means includes a substantially cylindrical lamp located within the drum means at substantially the rotation axis of the drum means.

4. The rotating fluidized bed reactor of claim 1, including inert solid particles within the drum means, that can optionally be combined with chemical reactant and the particles are of sufficient quantity to substantially cover the inner surface of the annular wall to form an annular bed of particles against the inner surface of the annular wall when the drum means is rotated and of insufficient quantity to completely fill the drum means, so that a void region that does not include particles will exist at substantially the rotation axis of the drum means, when the drum means is rotated.

5. The rotating fluidized bed reactor of claim 4, wherein the reactor includes electromagnetic radiation means for providing electromagnetic radiation to the interior of the drum means from the void region.

6. The rotating fluidized bed reactor of claim 5, wherein the rotation axis is substantially vertical and the annular wall is cone shaped so that the diameter of the annular wall increases from the bottom of the annular wall to the top of the annular wall.

7. The rotating fluidized bed reactor of claim 4, including a first reactant combined with the inert particles and a gas stream flowing through the annular wall and the bed of particles to fluidize the bed, wherein at least a portion of the gas stream includes a second gaseous reactant that reacts with the first reactant that is combined with the inert particles, to form a reaction product.

8. The rotating fluidized bed reactor of claim 5, including solids feed means and solids exit means for continuously adding and removing the inert solid particles from the bed as the drum means rotates.

9. The rotating fluidized bed reactor of claim 8, wherein the solids feed means includes a feed nozzle at substantially the top of the drum means and the solids exit means includes an exit port located at substantially the bottom of the drum means.

10. The rotating fluidized bed reactor of claim 7, wherein the solids feed means includes an inlet at substantially the bottom of the drum means and the solids exit means includes exit tubes extending through the annular wall.

11. The rotating fluidized bed reactor of claim 5, wherein the annular wall is formed of sintered metal.

12. The rotating fluidized bed reactor of claim 5, wherein the particles are between about 100 to 250 mesh.

13. The rotating fluidized bed reactor of claim 1, wherein the plenum means is constructed to deliver gas to the outer surface of the annular wall in a direction tangential to the annular wall.

14. A method of conducting a chemical reaction, comprising:
    providing a container having a first wall that is gas transmissive, the container having a rotation axis and being rotatable about the axis, the first wall positioned annularly about the axis;
    inserting into the container, inert solid particles that can be optionally combined with chemical reactant;
    rotating the container about the axis and spreading the particles against the first wall;
    flowing a gas stream through the first wall and through the particles, as the container rotates about the axis, to create a rotating fluidized bed of the particles against the first wall;
    exposing the bed of particles with electromagnetic radiation, from within the container.

15. The method of claim 14, wherein the particles are added continuously to the container and removed continuously from the container, as the container rotates.

16. The method of claim 15, wherein the particles are added continuously to the container and removed continuously from the container, as the container rotates.

17. The method of claim 15, wherein a first reactant is added to the particles prior to insertion within the container and the reactant is converted into a product within the container after exposure from the electromagnetic radiation.

18. The method of claim 14, wherein a first reactant is added to the inert particles prior to insertion within the container and a second gaseous reactant is included in the gas stream and the first reactant combines chemically with the second reactant to yield a reaction product.

19. The method of claim 15, wherein a gaseous reactant is included in the gas stream and the gaseous reactant is converted to a reaction product after exposure by the electromagnetic radiation.

20. The method of claim 15, wherein the container is rotated between about 200 and 1000 RPM.

21. The method of claim 15, wherein the reaction occurring within the container is selected from the group consisting of photochlorination, sulfochlorination of alkanes, sulfoxidation of alkanes, synthesis of Vitamin $D_3$, photooxygenation of cylclohexane and photonitrosation of cyclohexane and the catalytic cracking of petroleum compounds.

22. The method of claim 15, wherein dibenzyl ketone is converted to diphenyl ethane by adding dibenzyl ketone to the inert particles, flowing an effective amount of gas through the particles to form a fluidized bed of particles and exposing the particles with UV radiation.

23. The method of claim 15, wherein dehydrocholesterol is converted to previtamin $D_3$ by providing UV radiation within the container, combining the inert particles with dehydrocholesterol and flowing an inert gas through the particles.

24. The method of claim 15, wherein dodecane is converted to 1-chlorododecane by providing UV radiation within the container, the particles are ZSM-5 zeolite combined with dodecane and the gas stream includes chlorine.

25. The method of claim 14, wherein the gas stream includes biological organisms, the radiation source emits UV radiation and the gas stream is substantially purified after flowing through the particles.

26. The method of claim 14, including filtering material from the gas stream with the solid particles, wherein gas flows to the first wall tangentially with the tangential direction of rotation of the container.

27. The method of claim 26, wherein the gas stream includes biological organisms, the radiation source emits UV radiation and the gas stream is substantially purified after flowing through the particles.

28. The method of claim 14, wherein the temperature of the gas stream is controlled to control the kinetics of the reaction.

* * * * *